United States Patent [19]

Cole

[11] Patent Number: 5,700,842

[45] Date of Patent: Dec. 23, 1997

[54] METHODS OF INCORPORATING A HYDROPHOBIC SUBSTANCE INTO AN AQUEOUS SOLUTION

[75] Inventor: Douglas Bryan Cole, Appleton, Wis.

[73] Assignee: Kimberly-Clark Worldwide, Inc., Neenah, Wis.

[21] Appl. No.: 551,661

[22] Filed: Nov. 1, 1995

[51] Int. Cl.$^6$ .................................................. A61K 31/16
[52] U.S. Cl. ........................ 514/721; 514/943; 424/414; 424/443
[58] Field of Search ............................. 514/943, 721; 424/414, 443

[56] References Cited

U.S. PATENT DOCUMENTS

| | | | |
|---|---|---|---|
| 3,652,764 | 3/1972 | Lamberti et al. | 424/235 |
| 3,700,601 | 10/1972 | Bloching | 252/105 |
| 3,947,576 | 3/1976 | Kuczkowski et al. | 424/263 |
| 3,968,210 | 7/1976 | Schenkel | 424/235 |
| 3,989,827 | 11/1976 | Apostolatos et al. | 424/235 |
| 4,020,183 | 4/1977 | Asculai et al. | 424/341 |
| 4,100,324 | 7/1978 | Anderson et al. | 428/288 |
| 4,111,844 | 9/1978 | Polony et al. | 514/721 |
| 4,241,080 | 12/1980 | Burk | 424/304 |
| 4,355,021 | 10/1982 | Mahl et al. | 424/443 |
| 4,615,937 | 10/1986 | Bouchette | 424/443 |
| 4,643,939 | 2/1987 | Sugiyama et al. | 428/283 |
| 4,800,082 | 1/1989 | Karbowski et al. | 424/409 |
| 4,942,029 | 7/1990 | Scheps | 424/78 |
| 5,006,529 | 4/1991 | Resch | 514/721 |
| 5,080,901 | 1/1992 | Hangay et al. | 424/195.1 |
| 5,312,688 | 5/1994 | Honguu et al. | 428/395 |
| 5,403,587 | 4/1995 | McCue et al. | 514/943 |
| 5,403,864 | 4/1995 | Bruch et al. | 514/721 |
| 5,416,075 | 5/1995 | Carson et al. | 514/23 |
| 5,417,875 | 5/1995 | Nozaki et al. | 252/106 |
| 5,531,984 | 7/1996 | Staats | 424/443 |
| 5,550,145 | 8/1996 | Olund et al. | 514/396 |

FOREIGN PATENT DOCUMENTS

| | | | |
|---|---|---|---|
| 0 259 249 A3 | 3/1988 | European Pat. Off. | A01N 25/02 |
| 1943694 | 3/1971 | Germany. | |
| 25 46 951 A1 | 4/1976 | Germany | C11D 1/65 |
| 37 23 990 A1 | 2/1988 | Germany | A01N 31/14 |
| 1408885 | 10/1975 | United Kingdom. | |
| 2 211 093 | 6/1989 | United Kingdom | A01N 25/30 |
| WO 92/18100 A1 | 10/1992 | WIPO | A61K 7/50 |
| WO93/07250 | 4/1993 | WIPO. | |

OTHER PUBLICATIONS

Patent Cooperation Treaty Search Report from the International Search Authority, International Application No. PCT/US 96/16010 dated Mar. 20, 1997.

Derwent World Patent Database abstract of EP 259,249: Description of A. R. Cox et al., "Microbicidal Compositions."

Derwent World Patent Database abstract of DE 2,546,951: Description of Reckitt & Colmann Prod. Ltd., "Hair Shampoo Containing Polyethylene Imine Conditioner."

Derwent World Patent Database abstract of DE 3,723,990: Description of A. R. Cox et al., "Microbicidal Formation Used Especially For Skin Disinfection."

Derwent World Patent Database abstract of JP 2–152,916: Description of Clean Chemical Company, "Bactericidal Solution For Cleaning Dental Impression Material."

Copending U. S. Patent Application entitled "Antimicrobial Compositions And Wet Wipes Including The Same" and filed Nov. 1, 1995, in the name of Cole, Attorney Docket No. 12,351.

*Primary Examiner*—James H. Reamer
*Attorney, Agent, or Firm*—Jeffrey B. Curtin

[57] ABSTRACT

Methods of incorporating a hydrophobic substance into an aqueous solution in a manner which provides a homogeneous composition are described. The hydrophobic substance is at least partially dissolved in an amide to provide an active mixture. The active mixture is then combined with an aqueous solution to form a composition which may then be mixed for a sufficient amount of time to obtain a uniform dispersion. In a particular aspect, the aqueous solution may include a surfactant.

27 Claims, No Drawings

METHODS OF INCORPORATING A HYDROPHOBIC SUBSTANCE INTO AN AQUEOUS SOLUTION

BACKGROUND OF THE INVENTION

1. Field of the Invention

The present invention relates to methods of incorporating a hydrophobic substance into an aqueous solution. In particular, the present invention relates to methods of incorporating a hydrophobic antimicrobial agent into an aqueous solution in a manner which provides a homogeneous antimicrobial composition.

2. Description of the Related Art

It has been desirable to incorporate hydrophobic substances into aqueous solutions. For example, it has been desirable to incorporate hydrophobic antibacterial agents into aqueous solutions to provide antibacterial compositions which can be used in cleansing and cosmetic products such as liquid soaps, shampoos, detergents, lotions, and premoistened wipes. However, several problems have occurred when attempting to incorporate hydrophobic substances, such as hydrophobic antibacterial agents, into aqueous solutions.

For example, it has been very difficult to achieve a homogeneous or uniformly dispersed mixture when the hydrophobic substances are added to aqueous compositions. Frequently, the hydrophobic substance has undesirably precipitated in the aqueous compositions. Such non-homogeneous compositions have also resulted in compositions which have not been completely satisfactory to the consumer due to their cloudy appearance. In an attempt to solve this problem, several conventional compositions have included solvents, such as ethanol and propanol, to achieve solubility of the hydrophobic substance. However, conventional compositions which have included such solvents have undesirably resulted in dehydration, stinging and irritation of the skin of the user. The use of such solvents has also undesirably resulted in compositions which are highly unstable, relatively volatile, and difficult to process.

As a result, it has been necessary to use water soluble substances in many applications. For example, it has been necessary to use antibacterial agents which readily dissolve in water in many conventional antibacterial compositions. However, such water soluble antibacterial agents have not been completely satisfactory. For example, many of the water soluble antibacterial agents are not as antimicrobially effective as the hydrophobic antibacterial agents.

In an attempt to achieve homogeneous mixtures, many conventional compositions have also used large quantities of surface active agents, or surfactants. However, such large quantities of surfactants have lead to excessive foaming of the composition and compositions which are cloudy in appearance. Such excessive foaming and cloudy appearance of the compositions is generally undesirable to the consumer and is particularly undesirable to the consumer when the composition is being used in wet wipes. Typically, consumers of wet wipes desire solutions which do not lather, foam or deposit suds on the skin.

Accordingly, it remains desirable to provide compositions which are stable, highly effective, homogeneous and nonirritating to the skin. In particular, it remains desirable to provide methods for incorporating hydrophobic substances, such as hydrophobic antimicrobial agents, into aqueous solutions in a manner which provides a homogeneous composition. For example, it remains particularly desirable to incorporate hydrophobic antimicrobial agents into aqueous solutions to provide an antimicrobial, homogeneous, clear solution which is nonirritating to the skin and relatively nonlathering. It is also desirable that such homogeneous compositions be readily processable. Such methods are particularly desirable for incorporating hydrophobic antimicrobial agents into solutions for conventional wet wipes.

SUMMARY OF THE INVENTION

In response to the difficulties and problems discussed above, a new method of incorporating a hydrophobic substance into an aqueous solution in a manner which provides a homogeneous composition has been discovered. In particular, a new method of incorporating a hydrophobic antimicrobial agent into an aqueous solution in a manner which provides a homogeneous antimicrobial composition and an antimicrobial composition produced by such a method have been discovered.

As used herein, the term "amide" refers to an organic compound which contains the structural group —$CONH_2$. Suitable amides have the following structural formula:

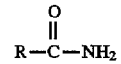

wherein R is a fatty alkyl group.

As used herein, the phrase "antimicrobial" refers to a composition which prevents the growth of *Escherichia coli* (ATCC #11229), *Staphylococcus aureus* (ATCC #6538) (both bacteria), and *Candida albicans* (ATCC #10231) (yeast) in a standard Minimum Inhibitory Concentration (MIC) test. Determining MIC values involves standard microbiological laboratory practices as described in the Examples. In general terms, the MIC value is determined by incubating the test organisms in the presence of various dilutions of the composition and monitoring the growth rate. The MIC value is the lowest concentration of the antimicrobial agent which inhibits the growth of the test organism.

As used herein, the term "aqueous" refers to a composition, solution or mixture which contains at least about 50 weight percent water, desirably at least about 70 weight percent water and more desirably at least about 90 weight percent water based on a total weight of the composition, solution or mixture.

As used herein, the term "homogeneous" refers to a composition, solution or mixture whose elements are substantially uniformly dispersed in each other. For example, a homogenous composition may include two or more compounds or elements which are substantially uniformly dispersed within each other. Desirably, the homogeneous composition is relatively clear in appearance. In addition, the homogenous composition desirably contains very minimal particulate matter. In one aspect, a homogenous composition is a composition which does not have any particulate matter having a size greater than about 1 micrometer.

As used herein, the term "hydrophobic" refers to a substance which is incapable of completely dissolving in an excess of water. In one aspect, a hydrophobic substance is a substance which does not completely dissolve in an excess of water when allowed to stand for a period of 24 hours.

In one aspect, the present invention concerns a method of incorporating a hydrophobic substance into an aqueous solution to provide a homogeneous composition. The method comprises at least partially dissolving the hydrophobic substance in an amide to form an active mixture and combining the active mixture with the aqueous solution to form the homogeneous composition.

In another aspect, the present invention concerns a method of making an aqueous antimicrobial composition comprising combining an active mixture with a surfactant/water mixture wherein said active mixture includes an effective amount of a hydrophobic antimicrobial agent and an amide. The active mixture may also be mixed and/or heated before combining it with the surfactant/water mixture. The resulting aqueous antimicrobial composition may also be mixed for an effective amount of time to make the solution homogeneous. In a particular embodiment, the aqueous antimicrobial composition includes at least about 50 weight percent water based on a total weight of the composition.

In another aspect, the present invention concerns a method of making a homogeneous antimicrobial composition comprising (a) at least partially dissolving from about 0.01 to about 3.0 weight percent of a hydrophobic antimicrobial agent based on a total weight of the composition in from about 1.0 to about 15.0 weight percent of an amide based on the total weight of the composition to form an active mixture; (b) blending from about 1.0 to 30.0 weight percent of a surfactant based on the total weight of the composition in from about 50 to about 98 weight percent water based on the total weight of the composition to form a surfactant/water mixture; and (c) combining the active mixture with the surfactant/water mixture to provide the homogeneous antimicrobial composition.

In yet another aspect, the present invention concerns a method of making a homogeneous antimicrobial composition comprising the steps of (a) at least partially dissolving from about 0.01 to about 3.0 weight percent 2,4,4'-trichloro-2'-hydroxydiphenyl ether based on a total weight of the composition in from about 1.0 to about 15.0 weight percent of a diethanolamide based on the total weight of the composition to form an active mixture; (b) blending less than about 10 weight percent of a nonionic surfactant based on the total weight of the composition in at least about 50 weight percent water based on the total weight of the composition to form a surfactant/water mixture; and (c) combining the active mixture with the surfactant/water mixture to provide the homogeneous antimicrobial composition.

In still another aspect, the present invention concerns a method of making an antimicrobial wet wipe comprising (a) providing an absorbent sheet; and (b) wetting the absorbent sheet with from about 150 to about 600 weight percent of an aqueous antimicrobial composition based on a dry weight of the wet wipe wherein the antimicrobial composition is made from a method comprising combining an active mixture with a surfactant/water mixture wherein said active mixture includes an effective amount of a hydrophobic antimicrobial agent and an amide. In a particular aspect, the aqueous antimicrobial composition includes at least about 50 weight percent water based on a total weight of the composition. In another particular aspect, the antimicrobial composition is made from a method comprising the steps of (i) at least partially dissolving from about 0.01 to about 3.0 weight percent of a hydrophobic antimicrobial agent based on a total weight of the composition in from about 1.0 to about 15.0 weight percent of an amide based on the total weight of the composition to form an active mixture; (ii) blending from about 1.0 to about 30.0 weight percent of a surfactant based on the total weight of the composition in from about 50 to about 98 weight percent water based on the total weight of the composition to form a surfactant/water mixture; and (iii) combining the active mixture with the surfactant/water mixture to provide the homogeneous antimicrobial composition.

In yet another aspect, the present invention concerns an antimicrobial composition and an antimicrobial wet wipe made by the method aspects of the present invention.

Accordingly, the present invention advantageously provides a method of incorporating a hydrophobic substance into an aqueous solution in a manner which provides a homogeneous composition. In particular, the present invention advantageously provides a method of making a highly aqueous, antimicrobial composition which includes a hydrophobic antimicrobial agent and a relatively large percentage of water. The invention further provides improved processes for incorporating hydrophobic antimicrobial agents in aqueous solutions without the use of solvents which are volatile and highly flammable.

DETAILED DESCRIPTION OF THE INVENTION

The present invention concerns improved methods of incorporating a hydrophobic substance into an aqueous solution. In particular, the present invention concerns improved methods of incorporating a hydrophobic antimicrobial agent into an aqueous solution to provide a homogeneous antimicrobial composition and an antimicrobial composition made by such methods. The different method aspects of the present invention will be described for use in incorporating hydrophobic antimicrobial agents into aqueous solutions to provide antimicrobial compositions for use in conventional wet wipes. However, it is to be understood, that such methods and the resulting compositions may be used to incorporate other hydrophobic substances such as, for example, surfactants, emulsifiers, emollients, oils, and the like, into aqueous solutions which may be used in the manufacture of other consumer products such as, for example, shampoos, soaps, cleansing agents, detergents, lotions and the like.

It has been discovered that hydrophobic substances, such as hydrophobic antimicrobial agents, may be used in aqueous solutions to provide homogeneous compositions if the compositions are prepared according to the methods of the present invention. According to the different method aspects of the present invention, an antimicrobial composition is prepared by a method which involves combining an active mixture of a hydrophobic antimicrobial agent and an amide with an aqueous solution, such as a mixture of water and a surfactant. In a particular aspect of the invention, the homogeneous antimicrobial composition is prepared by a method which involves at least partially dissolving an effective amount of the hydrophobic antimicrobial agent in the amide to form the active mixture and separately blending the water and surfactant together to form a surfactant/water mixture. The active mixture is then combined with the surfactant/water mixture to provide the antimicrobial composition.

The hydrophobic antimicrobial agent is at least partially dissolved and, desirably, completely dissolved in the amide before the active mixture is combined with the aqueous solution. For example, the active mixture may be mixed for a period of time to ensure the hydrophobic antimicrobial agent is substantially dissolved in the amide. In a particular aspect, the active mixture may be mixed for at least about 10 minutes, desirably at least about 20 minutes, and more desirably at least about 30 minutes to effectively dissolve most of the hydrophobic antimicrobial agent in the amide. Alternatively, the active mixture may be allowed to stand for a sufficient period of time to at least partially dissolve the hydrophobic antimicrobial agent in the amide. The active mixture may also be heated to dissolve at least a portion of the hydrophobic antimicrobial agent in the amide before the active mixture is combined with the aqueous solution. For example, the active mixture may be heated to a temperature of from about 30 to about 50 degrees Centigrade and desirably from about 37 to about 45 degrees Centigrade to effectively dissolve the hydrophobic antimicrobial agent in the amide. In a particular aspect, the hydrophobic antimicrobial agent is dissolved in the amide such that the active mixture does not contain any particulate matter having a size greater than about 1.0 micrometers. Desirably, the active mixture does not contain any particulate matter having a size greater than about 0.50 micrometers and, more desirably, the active mixture does not contain any particulate matter having a size greater than about 0.14 micrometers.

After the active mixture has been combined with the aqueous solution, the antimicrobial composition may also be mixed for an effective amount of time to make the composition relatively homogeneous and substantially reduce the size and number of insoluble particulates. For example, the antimicrobial composition may be mixed for at least about 5 minutes and desirably at least about 10 minutes to provide a relatively clear, homogeneous antimicrobial composition.

A wide range of hydrophobic antimicrobial agents which provide antimicrobial compositions may be used in the different aspects of the present invention. The antimicrobial composition may include a single hydrophobic antimicrobial agent or a combination of two or more hydrophobic antimicrobial agents. Desirably, the hydrophobic antimicrobial agent is a broad spectrum antimicrobial agent. For example, suitable hydrophobic antimicrobial agents include triclosan, triclocarban, and the like, and combinations thereof. Such hydrophobic antimicrobial agents are generally considered to be water insoluble by those skilled in the art. In a particular aspect, the antimicrobial composition includes triclosan to provide improved antimicrobial effectiveness. As used herein, the term "triclosan" refers to 2,4,4'-trichloro-2'-hydroxydiphenyl ether.

The hydrophobic antimicrobial agent may be present in the composition in any amount which provides an antimicrobial composition. However, if the amount of the hydrophobic antimicrobial agent is too high, the composition may be unclear and irritating to the skin of the user. Moreover, if the amount of the hydrophobic antimicrobial agent is too low, the composition may not be antimicrobially effective as described herein. As set forth above, the antimicrobial effectiveness of the antimicrobial composition can be determined by testing the composition against several known microorganisms. It has been found that antimicrobial compositions of the present invention which include from about 0.01 to about 3.0 weight percent, desirably from about 0.03 to about 1.0 weight percent, and more desirably from about 0.05 to about 0.7 weight percent of the hydrophobic antimicrobial agent based on the total weight of the composition are effective against most microorganisms while not irritating the skin. It has also been found that the antimicrobial composition of the different aspects of the present invention is particularly effective when it contains from about 0.01 to about 3.0 weight percent and more desirably from about 0.03 to about 1.0 weight percent triclosan based on the total weight of the composition.

The antimicrobial composition of the different aspects of the present invention may also include other antimicrobial agents which may or may not be considered hydrophobic. For example, the antimicrobial composition may also include p-chloro-m-xylenol, benzalkonium chloride, chlorohexidine gluconate, hexachlorophene, and the like, and combinations thereof.

A wide range of amides which at least partially dissolve the hydrophobic antimicrobial agents may be used in the different aspects of the present invention. For example, suitable amides include alkanolamides, long chain fatty acid diethanolamides, long chain fatty acid monoethanolamides, monoisopropanolamides, and the like, and combinations thereof. In a particular aspect, the amide includes at least about 50 weight percent and desirably at least about 90 weight percent of a lauric diethanolamide based on a total weight of the amide. It has been discovered that the use of a lauric diethanolamide is particularly desirable because of it's solubility in water.

The amide may be present in the antimicrobial composition in any amount which provides the desired composition. However, if the amount of the amide is too high, the composition may be irritating to the skin of the user. Moreover, if the amount of the amide is too low, the hydrophobic antimicrobial agent may not dissolve and the composition may not be homogeneous. It has been found that antimicrobial compositions which include from about 1.0 to about 15.0 weight percent, desirably from about 2.0 to about 10.0 weight percent and more desirably from about 3.0 to about 5.0 weight percent of the amide based on the total weight of the composition are effective. It has also been found that the antimicrobial composition of the different aspects of the present invention is particularly effective when it contains from about 2.0 to about 10.0 and more desirably from about 3.0 to about 5.0 weight percent of an alkanolamide based on the total weight of the composition.

A wide range of surfactants may also be incorporated into the aqueous solution of the different aspects of the present invention. It has been hypothesized that the surfactant acts to prevent the precipitation of the active mixture of the hydrophobic antimicrobial agent and amide in the water. Suitable surfactants include those which prevent such precipitation. For example, suitable surfactants may include anionic surfactants, nonionic surfactants, cationic surfactants, amphoteric surfactants and combinations thereof as are well known to those skilled in the art. Suitable anionic surfactants include sodium laureth sulfate, sodium-lauryl methyl taurate, myristoyl sarcosine, sodium dodecylbenzene sulfonate, and the like.

Suitable nonionic surfactants include the polyoxyethylene ethers of the higher fatty alcohols and alkyl phenols; the polyethylene glycols of fatty acids; fatty alkylol amide condensation products; polymers of ethylene and propylene oxides; compounds formed by the addition of propylene oxide to ethylene diamide, followed by the addition of ethylene oxide; fatty acid ethylene oxide condensation products; ethoxylate carboxylic acid; ethoxylate glycerides; and glycol esters. In a particular aspect, the surfactant is desirably a nonionic surfactant, such as octoxynol-9, which provides an improved composition because of it's solubility in water and low level of irritation to the skin.

The surfactant may be present in the aqueous solution and antimicrobial composition in any amount which provides the desired composition. However, if the amount of the surfactant is too high, the composition may be unclear and cause excessive foaming. Moreover, if the amount of the surfactant is too low, the active mixture may precipitate and the composition may not be homogeneous. It has been found that the antimicrobial compositions of the present invention which include from about 1.0 to about 30.0 weight percent, desirably from about 1.0 to about 20.0 weight percent and more desirably from about 4.0 to about 10 weight percent of the surfactant based on the total weight of the composition are effective. If it is desired to use the antimicrobial composition in a wet wipe or similar product, the amount of surfactant should not cause excessive foaming of the composition. For example, antimicrobial compositions according to the present invention which include less than about 10.0 weight percent and desirably less than about 7.0 weight percent of the surfactant based on the total weight of the composition have been found to be particularly effective with wet wipes.

The antimicrobial compositions may also include additional elements such as, for example, emollients, perfuming agents, chelating agents, cleansing agents, foam stabilizers, preservatives, protectants, and the like, to enhance the performance of the compositions.

Accordingly, the different aspects of the present invention provides antimicrobial compositions which include hydrophobic antimicrobial agents in an aqueous environment. In a particular aspect, the composition of the present invention defines an MIC value of 100 ppm (parts per million active) or less against E. coli (ATCC #11229) and S. aureus (ATCC #6538) (both bacteria), and an MIC value of 10,000 ppm or less against C. albicans (ATCC #10231) (yeast), desirably defines an MIC value of 10 ppm or less against E. coli (ATCC #11229) and S. aureus (ATCC #6538) (both bacteria), and an MIC value of 1,000 ppm or less against C. albicans (ATCC #10231) (yeast), and more desirably defines an MIC value of 1 ppm or less against E. coli (ATCC #11229) and S. aureus (ATCC #6538) (both bacteria), and an MIC value of 1,000 ppm or less against C. albicans (ATCC #10231) (yeast). Such aqueous antimicrobial compositions are particularly useful in premoistened wipes and cosmetic products such as liquid soaps, shampoos, and lotions.

In another aspect, the present invention concerns an antimicrobial wet wipe and methods of making antimicrobial wet wipes which include the antimicrobial compositions described herein. The antimicrobial wet wipes may appear in several different forms. For example the wet wipes may be in the form of a stack of moistened sheets which have been packaged in a plastic container. The wet wipes may also be in a folded or unfolded configuration. In addition, the wet wipes may be in the form of continuous webs of material which include perforations to separate the individual wet wipes from the continuous web. Such continuous webs may be wound into rolls and also packaged in plastic containers. Such wet wipes can be used for baby wipes, hand wipes, household cleaning wipes, industrial wipes and the like.

The particular method and sequence of steps to manufacture antimicrobial wet wipes described herein is not a limitation to the present invention, but is disclosed only as one method of producing a wet wipe. Initially, a supply roll of the material being converted into the wet wipe is unwound to provide a continuously moving web of material. The web of material is saturated or otherwise impregnated with the antimicrobial compositions of the present invention, as described herein, by any suitable means such as spraying, dipping, or the like as are well known to those skilled in the art. In a particular aspect, the web of material is passed over several perforated tubes which exude the antimicrobial composition into the material. The amount of the antimicrobial composition which may be added to the material may vary depending upon the type of material being used to provide the wet wipe, the type of container being used to store the wet wipes, and the desired end use of the wet wipe. Generally, each wet wipe can contain from about 150 to about 600 weight percent and desirably from about 250 to about 450 weight percent of the antimicrobial composition based on the dry weight of the wipe. In a particular aspect wherein the wet wipe is made from a coform material comprising from about 30 to about 40 weight percent polymeric microfibers based on the dry weight of the wipe, the amount of the antimicrobial composition contained within the wet wipe is from about 300 to about 400 weight percent and desirably about 330 weight percent based on the dry weight of the wet wipe. If the amount of liquid is less than the above-identified range, the wet wipe may be too dry and may not adequately perform. If the amount of liquid is greater than the above-identified range, the wet wipe may be oversaturated and soggy and the liquid may pool in the bottom of the container.

The web of material is then slit in the machine direction into multiple ribbons, each of which may be folded into the type of fold desired for the individual wet wipe. For example, the web of material can be slit into eight ribbons which may then be folded into a folded configuration. Each folded ribbon may then be combined, one ribbon on top of the other, with the other seven folded ribbons from the same web of material to form a continuous "sausage." The sausage is then cut into "clips" of eight wet wipes apiece and the clips of wet wipes are arranged in a stacked configuration to form at least one stack of antimicrobial wet wipes which is then placed in a plastic container.

Materials suitable for the antimicrobial wet wipe of the present invention are well known to those skilled in the art. The wet wipe can be made from any material suitable for use as a moist wipe, including meltblown, coform, air-laid, bonded-carded web materials, hydroentangled materials and the like and can comprise synthetic or natural fibers or combinations thereof. The wet wipe may have a basis weight of from about 25 to about 120 grams per square meter and desirably from about 40 to about 90 grams per square meter. In a particular aspect, the wet wipe is a coform basesheet of polymeric microfibers and cellulosic fibers having a basis weight of from about 60 to about 80 grams per square meter and desirably about 75 grams per square meter. Such coform basesheets are manufactured generally as described in U.S. Pat. No. 4,100,324 to Anderson et al. which issued Jul. 11, 1978, and which is herein incorporated by reference.

Typically, such coform basesheets comprise a gas-formed matrix of thermoplastic polymeric meltblown microfibers, such as, for example, polypropylene microfibers, and cellulosic fibers, such as, for example, wood pulp fibers. The relative percentages of the polymeric microfibers and cellulosic fibers in the coform basesheet can vary over a wide range depending on the desired characteristics of the wet wipes. For example, the coform basesheet may comprise from about 20 to about 100 weight percent, desirably from about 20 to about 60 weight percent, and more desirably from about 30 to about 40 weight percent of polymeric microfibers based on the dry weight of the coform basesheet being used to provide the wet wipe. Alternatively, the wet wipe 22 can be made from a meltblown sheet of polymeric microfibers having a basis weight of from about 25 to about 120 grams per square meter.

Accordingly, the different aspects of the present invention can also advantageously provide an antimicrobial wet wipe which, when compared to conventional wet wipes, has improved antimicrobial effectiveness and is nonirritating to the user. In particular, the different aspects of the present invention can provide an antimicrobial wet wipe which is wetted with an aqueous antimicrobial composition which includes a hydrophobic antimicrobial agent. Such wet wipes can advantageously be used for baby wipes, hand wipes, face wipes, cosmetic wipes, household wipes, industrial wipes and the like.

EXAMPLES

The following examples are presented to provide a more detailed understanding of the invention. The particular materials and parameters are exemplary and are not intended to limit the scope of the invention.

Example 1

An antimicrobial composition according to the present invention was prepared as follows. The composition included, based on a total weight of the composition, 1.0 weight percent triclosan (2,4,4'-trichloro-2'-hydroxydiphenyl ether), 4.0 weight percent lauric diethanolamide (Lauramide DEA), 8.0 weight percent Octoxynol-9 (CTFA nomenclature) and the remainder water. The triclosan was added to the lauric diethanolamide and the resulting mixture was heated to about 37.7 degrees Centigrade and mixed for about 15 minutes until clear. The water and Octoxynol-9 were blended together. The mixture of triclosan and lauric diethanolamide was then added to the water mixture and mixed for about 10 minutes. The resulting composition was very clear.

The composition was then subjected to the Minimum Inhibitory Concentration (MIC) technique to determine the lowest concentration of the composition which demonstrated a lower growth rate than the growth of the control against *E. coli* (ATCC #11229), *S. aureus* (ATCC #6538) (both bacteria), and *C. albicans* (ATCC #10231) (yeast). The protocol used to determine the MIC values was a standard microdilution method in a 96 well microplate format. Formulations were prepared by serially diluting each sample of the composition in sterile distilled water at dilutions of 0.01, 0.10, 1.0, 10, 100, and 1000 ppm (parts per million triclosan). The microplate wells were filled with the diluted formulation, a fixed number of microorganisms, and growth media (Mueller Hinton II for *E. coli* and *S. aureus* and Saboraud-Dextrose for *C. albicans*). The inoculums for *E. coli, S. aureus*, and *C. albicans* contained $1.3 \times 10^9$ CFU/ml, $4.9 \times 10^8$ CFU/ml, and $1.0 \times 10^7$ CFU/ml, respectively. The microplate was incubated in a THERMOmax™ microplate reader, which was commercially available from Molecular Devices Corporation, a business having offices located in Menlo Park, Calif. under the model numbers 0200–0600 and 0200–0601, for 18 hours at 37 degrees Centigrade. The plate reader was programmed to take optical density readings at 650 nanometers every 30 minutes to monitor the growth rate.

The composition had an MIC value of 1.0 ppm against *E. coli*, 0.1 ppm against *S. aureus* and 1000 ppm against *C. albicans*. The MIC value is the lowest concentration of the composition which demonstrates a slower growth rate than the positive growth control for each microorganism. The control was the same as the composition tested except that it did not include the triclosan. The control did not exhibit any antimicrobial activity at any dilution tested.

Example 2

An antimicrobial composition according to the present invention was prepared as follows. The composition included, based on a total weight of the composition, 0.5 weight percent triclosan (2,4,4'-trichloro-2'-hydroxydiphenyl ether), 4.0 weight percent lauric diethanolamide (Lauramide DEA), 5.0 weight percent Octoxynol-9 and the remainder water. The triclosan was added to the lauric diethanolamide and the resulting mixture was heated to about 37.7 degrees Centigrade and mixed for about 15 minutes until clear. The water and Octoxynol-9 were blended together. The mixture of triclosan and lauric diethanolamide was then added to the water mixture and mixed for about 10 minutes. The resulting composition was very clear.

Example 3

An antimicrobial composition according to the present invention was prepared as follows. The composition included, based on a total weight of the composition, 0.5 weight percent triclosan (2,4,4'-trichloro-2'-hydroxydiphenyl ether), 3.0 weight percent lauric diethanolamide (Lauramide DEA), 5.0 weight percent Octoxynol-9 and the remainder water. The triclosan was added to the lauric diethanolamide and the resulting mixture was heated to about 37.7 degrees Centigrade and mixed for about 15 minutes until clear. The water and Octoxynol-9 were blended together. The mixture of triclosan and lauric diethanolamide was then added to the water mixture and mixed for about 10 minutes. The resulting composition was slightly hazy.

Example 4

An antimicrobial composition according to the present invention was prepared as follows. The composition included, based on a total weight of the composition, 0.5 weight percent triclosan (2,4,4'-trichloro-2'-hydroxydiphenyl ether), 2.0 weight percent lauric diethanolamide (Lauramide DEA), 5.0 weight percent Octoxynol-9 and the remainder water. The triclosan was added to the lauric diethanolamide and the resulting mixture was heated to about 37.7 degrees Centigrade and mixed for about 15 minutes until clear. The water and Octoxynol-9 were blended together. The mixture of triclosan and lauric diethanolamide was then added to the water mixture and mixed for about 10 minutes. The resulting composition was clear.

Example 5

An antimicrobial composition according to the present invention was prepared as follows. The composition included, based on a total weight of the composition, 0.5 weight percent triclosan (2,4,4'-trichloro-2'-hydroxydiphenyl ether), 3.0 weight percent lauric diethanolamide (Lauramide DEA), 5.0 weight percent Disodium capryloamphodipropionate and the remainder water. The triclosan was added to the lauric diethanolamide and the resulting mixture was heated to about 37.7 degrees Centigrade and mixed for about 15 minutes until clear. The water and Disodium capryloamphodipropionate were blended together. The mixture of triclosan and lauric diethanolamide was then added to the water mixture and mixed for about 10 minutes. The resulting composition was cloudy and an additional 5.0 weight percent Disodium capryloamphodipropionate was added to achieve a clear solution.

Example 6

An antimicrobial composition according to the present invention was prepared as follows. The composition included, based on a total weight of the composition, 0.5 weight percent triclosan (2,4,4'-trichloro-2'-hydroxydiphenyl ether), 1.0 weight percent lauric diethanolamide (Lauramide DEA), 1.0 weight percent ricinoleamide (Ricinoleamide DEA), 5.0 weight percent Octoxynol-9 and the remainder water. The triclosan was added to the lauric diethanolamide and ricinol diethanolamide and the resulting mixture was heated to about 37.7 degrees Centigrade and mixed for about 15 minutes until clear. The water and Octoxynol-9 were blended together. The mixture of triclosan and lauric diethanolamide and ricinoleamide was then added to the water mixture and mixed for about 10 minutes. The resulting composition was very clear.

The examples representatively show that the different method aspects of the present invention can be used to incorporate hydrophobic antimicrobial agents in aqueous solutions to provide homogeneous antimicrobial solutions.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

I claim:

1. A method of incorporating a hydrophobic antimicrobial agent into an aqueous solution comprising at least partially dissolving said hydrophobic substance in an amide to form an active, homogeneous mixture and combining said active mixture with said aqueous solution to form a homogeneous composition, wherein said amide has the following structural formula:

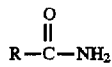

wherein R is a fatty alkyl group.

2. The method of claim 1 and further comprising mixing said active mixture before combining said active mixture with said aqueous solution.

3. The method of claim 1 and further comprising heating said active mixture before combining said active mixture with said aqueous solution.

4. The method of claim 1 wherein said aqueous solution includes at least about 50 weight percent water based on a total weight of said composition.

5. The method of claim 1 wherein said aqueous solution includes at least about 70 weight percent water based on a total weight of said composition.

6. The method of claim 1 wherein said aqueous solution includes a surfactant.

7. The method of claim 1 wherein said active mixture includes from about 0.01 to about 3.0 weight percent of said hydrophobic antimicrobial agent based on a total weight of said composition and from about 1.0 to about 15.0 weight percent of said amide based on the total weight of said composition.

8. A method of making an aqueous antimicrobial composition comprising combining an active, homogeneous mixture which includes an effective amount of a hydrophobic antimicrobial agent and an amide with a surfactant/water mixture to provide said aqueous antimicrobial composition, wherein said amide has the following structural formula:

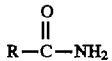

wherein R is a fatty alkyl group.

9. The method of claim 8 and further comprising mixing said active mixture before combining said active mixture with said surfactant/water mixture.

10. The method of claim 9 wherein said mixing includes mixing said active mixture for at least about 10 minutes.

11. The method of claim 8 and further comprising heating said active mixture before combining said active mixture with said surfactant/water mixture.

12. The method of claim 11 wherein said heating includes heating said active mixture to a temperature of from about 30 to about 50 degrees Centigrade.

13. The method of claim 8 and further comprising mixing said aqueous antimicrobial composition for an effective amount of time to make said composition homogeneous.

14. The method of claim 13 wherein said mixing of said aqueous antimicrobial composition includes mixing said composition for at least about 5 minutes.

15. The method of claim 13 wherein said mixing of said aqueous antimicrobial composition includes mixing said composition until said composition contains relatively no insoluble particles.

16. The method of claim 8 wherein said aqueous antimicrobial composition includes at least about 50 weight percent water based on a total weight of said composition.

17. A method of making a homogeneous antimicrobial composition comprising:

a) at least partially dissolving from about 0.01 to about 3.0 weight percent of a hydrophobic antimicrobial agent based on a total weight of said composition in from about 1.0 to about 15.0 weight percent of an amide based on the total weight of said composition to form an active, homogeneous mixture, wherein said amide has the following structural formula:

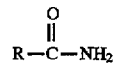

wherein R is a fatty alkyl group;

b) blending from about 1.0 to about 30.0 weight percent of a surfactant based on the total weight of said composition in from about 50 to about 98 weight percent water based on the total weight of said composition to form a surfactant/water mixture; and c) combining said active mixture with said surfactant/water mixture to provide said homogeneous antimicrobial composition.

18. The method of claim 17 and further comprising mixing said active mixture before combining said active mixture with said surfactant/water mixture.

19. The method of claim 17 and further comprising heating said active mixture before combining said active mixture with said surfactant/water mixture.

20. The method of claim 17 further comprising mixing said homogeneous antimicrobial composition for at least about 5 minutes.

21. A method of making a homogeneous antimicrobial composition comprising the steps of:

a) at least partially dissolving from about 0.01 to about 3.0 weight percent 2,4,4'-trichloro-2'-hydroxydiphenyl ether based on a total weight of said composition in from about 1.0 to about 15.0 weight percent of a diethanolamide based on the total weight of said composition to form an active, homogeneous mixture;

b) blending less than about 10 weight percent of a nonionic surfactant based on the total weight of said composition in at least about 50 weight percent water based on the total weight of said composition to form a surfactant/water mixture; and c) combining said active mixture with said surfactant/water mixture to provide said homogeneous antimicrobial composition. composition for at least about 5 minutes.

22. An antimicrobial composition made by the method of claim 8.

23. A method of making an antimicrobial wet wipe comprising:

a) providing an absorbent sheet; and b) wetting said absorbent sheet with from about 150 to about 600 weight percent of an aqueous antimicrobial composition based on a dry weight of said wet wipe wherein said antimicrobial composition is made from a method comprising combining an active, homogeneous mixture which includes an effective amount of a hydrophobic antimicrobial agent and an amide with a surfactant/water mixture, wherein said amide has the following structural formula:

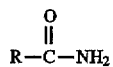

wherein R is a fatty alkyl group.

24. The method of claim 23 wherein said aqueous antimicrobial composition includes at least about 50 weight percent water based on a total weight of said composition.

25. A method of making an antimicrobial wet wipe comprising:
 a) providing an absorbent sheet; and
 b) wetting said absorbent sheet with from about 150 to about 600 weight percent of a homogeneous antimicrobial composition based on a total weight of said wet wipe wherein said antimicrobial composition is made from a method comprising the steps of:
  i) at least partially dissolving from about 0.01 to about 3.0 weight percent of a hydrophobic antimicrobial agent based on a total weight of said composition in from about 1.0 to about 15.0 weight percent of an amide based on the total weight of said composition to form an active, homogeneous mixture, wherein said amide has the following structural formula:

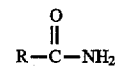

wherein R is a fatty alkyl group;
  ii) blending from about 1.0 to 30.0 weight percent of a surfactant based on the total weight of said composition in from about 50 to about 98 weight percent water based on the total weight of said composition to form a surfactant/water mixture; and
  iii) combining said active mixture with said surfactant water mixture to provide said homogeneous antimicrobial composition.

26. The method of claim 25 wherein said hydrophobic antimicrobial agent is 2,4,4'-trichloro-2'-hydroxydiphenyl ether.

27. An antimicrobial wet wipe made by the method of claim 23.

* * * * *